United States Patent [19]

Shibata et al.

[11] Patent Number: 4,578,034
[45] Date of Patent: Mar. 25, 1986

[54] DENTAL HANDPIECE HAVING AN OPTICAL FIBERSCOPE

[75] Inventors: Yuichi Shibata; Tadashi Baba, both of Kanuma, Japan

[73] Assignee: Nakanishi Dental Mfg. Co., Ltd., Kanuma, Japan

[21] Appl. No.: 646,210

[22] Filed: Aug. 31, 1984

[30] Foreign Application Priority Data

Aug. 31, 1983 [JP]  Japan ............................ 58-134597[U]

[51] Int. Cl.$^4$ .............................................. A61C 3/00
[52] U.S. Cl. ...................................... 433/29; 433/126
[58] Field of Search ................... 433/126, 29, 127, 129

[56] References Cited

U.S. PATENT DOCUMENTS

| | | | |
|---|---|---|---|
| 3,631,597 | 9/1969 | Lieb et al. | 433/126 |
| 4,104,799 | 8/1978 | Leonard | 433/129 |
| 4,202,102 | 5/1980 | Nakanishi | 433/127 |
| 4,260,382 | 4/1981 | Thomson | 433/126 |
| 4,398,885 | 8/1983 | Loge et al. | 433/29 |
| 4,403,956 | 9/1983 | Nakanishi | 433/29 |
| 4,403,959 | 9/1983 | Hatakeyama | 433/126 |
| 4,431,412 | 2/1984 | Lares et al. | 433/29 |

Primary Examiner—John J. Wilson
Attorney, Agent, or Firm—Wenderoth, Lind & Ponack

[57] ABSTRACT

A dental handpiece has a handle portion including a powerhead assembly integrally supported on a front end of the handle portion and a base cylindrical member located in a cylindrical hollow portion of the handle portion. The base cylindrical member has a first axial central passage for a fiberscope, a second side passage for supplying air under pressure, a third side passage for supplying water and a fourth passage for exhaust. A middle connector has a large diameter front hollow portion and a small diameter rear hollow portion having internal threads, three radial openings provided through the connector at equally spaced locations, passages corresponding to the passages in the base cylindrical member and a tubular plunger slidably mounted thereon. A driven ball and a driving ball are slidably located in each radial opening for engaging a circumferential slot around an external rear end portion of a hollow mount insert threadedly fitted into the rear end portion of the base cylindrical member. A rear connector has passages corresponding to those of the base cylindrical member and the middle connector. An electric lamp is located in the larger diameter front hollow portion of the middle connector and has a plurality of fluid pressure passages for removing heat from the electric lamp. The tubular plunger is slidably movable for radially displacing the driven and driving balls to disconnect or assemble the dental handpiece.

2 Claims, 4 Drawing Figures

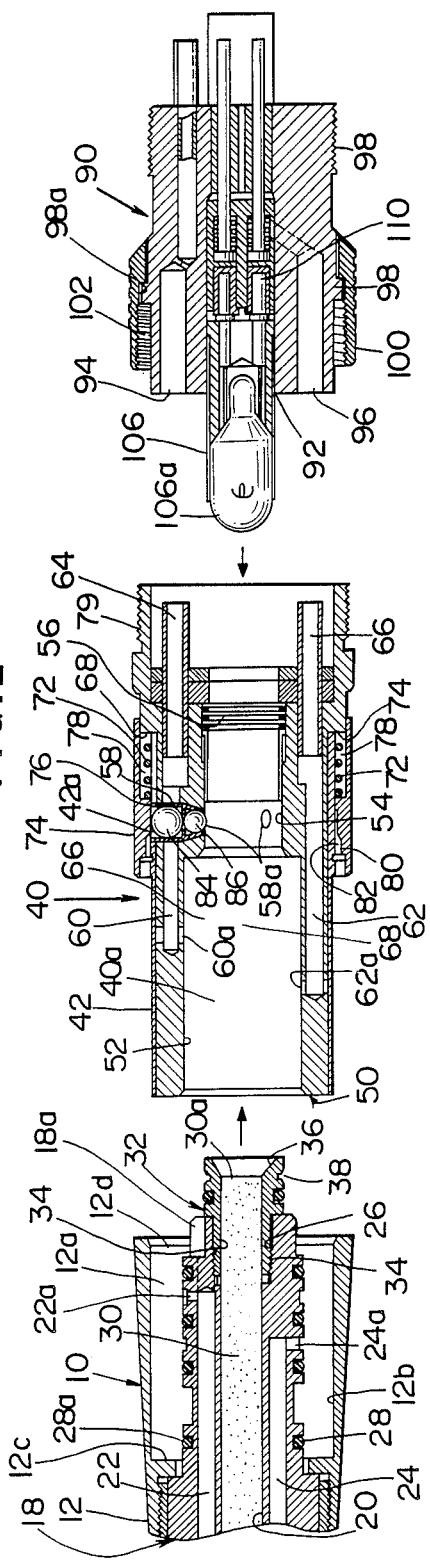
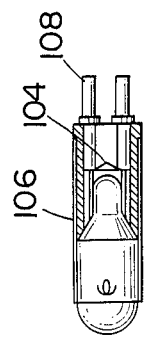

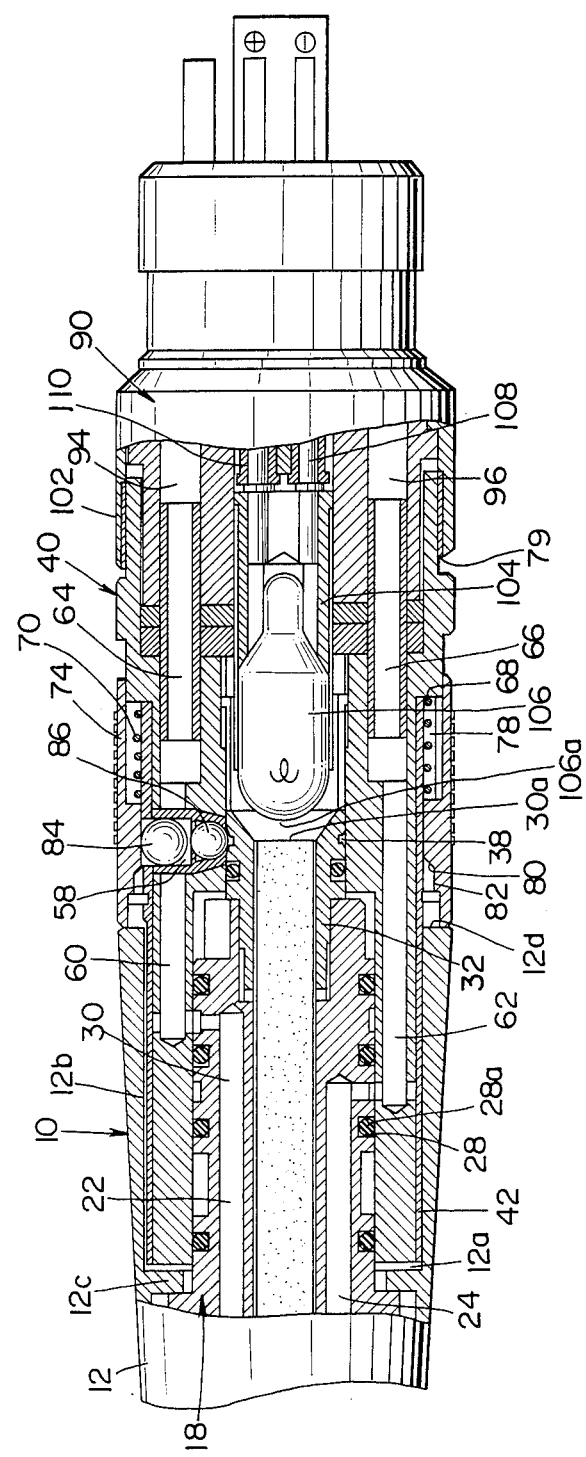

DENTAL HANDPIECE HAVING AN OPTICAL FIBERSCOPE

BACKGROUND OF THE INVENTION

This invention relates to improvements in a dental handpiece having an optical fiberscope which enables a dentist to disconnect a middle connecting means and a rear connecting means from a base cylindrical member or to join them easily and quickly.

In the conventional dental handpiece including an optical fiberscope and an electric lamp, a base cylindrical member, a middle connecting means and a rear connecting means are rigidly connected so that it is very difficult to disassemble or assemble the handpiece quickly, and heat produced from the electric lamp can not be removed.

OBJECTS OF THE INVENTION

A principal object of this invention is to provide a dental handpiece having an optical fiberscope built in a handle portion whereby the handle portion, a middle connecting means and a rear connecting means are relatively rotatably and detachably connected with each other in such a way as to make it possible to disassemble or assemble the dental handpiece easily and quickly.

Another object of this invention is to provide a dental handpiece having an optical fiberscope built in a handle portion whereby an electric lamp in the rear connecting means can be exchanged easily and quickly.

Another object of this invention is to provide a dental handpiece including an electric lamp which is axially centrally located in the rear connecting means, and when coupled, the electric lamp is surrounded with a plurality of fluid pressure passages in the middle connecting means so as to remove heat released from the electric lamp.

A further object of this invention is to provide a dental handpiece which can be easiliy and quickly maintained by oiling and performing repairs.

A still further object of this invention is to provide a device suitable for the aforementioned purposes which will have a comparatively simple construction and at the same time be sufficiently rigid, strong and durable.

BRIEF DESCRIPTION OF DRAWING

While we have shown in the accompanying drawings, a preferred embodiment of our invention, it should be understood that the same is susceptible of modification and change without departing from the spirit of our invention.

FIG. 2 is a greatly enlarged vertical sectional view of the dentral handpiece shown in FIG. 1;

FIG. 3 is a front elevation of an electric lamp to be inserted into a jack of the rear connecting means; and FIG. 4 is a greatly enlarged vertical sectional view of the assembled handle portion, middle connecting means and rear connecting means shown in FIGS. 1-3.

DETAILED DESCRIPTION OF THE PREFERRED EMBODIMENT

Figure 1:
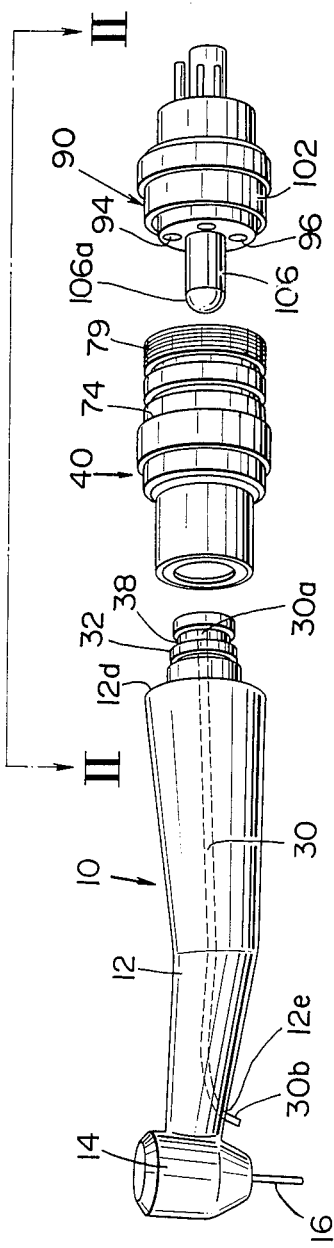
FIG. 1 is an exploded perspective view of a preferred embodiment of the dental handpiece of this invention, and showing a fiber optics bundle in dotted lines.

Referring to the accompanying drawings, the dental handpiece 10 of this invention comprises a handle portion 12 and a powerhead assembly 14 which is integrally supported on a front end of the handle portion 12. At the top end the powerhead assembly 14 is an air turbine (not shown) which operates, when energized, to rotate at high speed a dental tool shown at 16.

A small opening 12e is provided at a bottom portion of the handle portion 12 adjacent the powerhead assembly 14, and an inturned transverse annular flange 12c is formed around an inner circumferential surface 12b near an inlet portion 12d thereof.

A first passage 20 for a fiberscope 30 is axially and centrally provided to extend through a substantial length of a base cylindrical member 18 of handle portion 12, a second passage 22 for introducing air under pressure, a third passage 24 for supplying water and a fourth passage for exhaust (not shown) are axially provided near and around the central passage 20 and also lengthwise along the base cylindrical member 18. A radial bore 22a and a radial bore 24a are provided near a read end portion of the cylindrical member 18 intersecting the second passage 22 and the third passage 24 respectively.

In the outer surface of the cylindrical wall of the base cylindrical member 18, at axially spaced locations, are circumferential slots 28, into each of which a separate seal ring 28a is respectively fitted, and a detent 18a is provided at an upper peripheral end portion of the base cylindrical member 18. Also provided are screw threads 34 around the inner periphery of the central passage 20 near an end portion thereof.

The fiberscope 30 consisting of extremely fine filaments of glass extending axially through the central passage 20 of the cylindrical member 18, and its rear end projects slightly out of the end portion of the central passage 20. The base cylindrical member 18 extends into a cylindrical hollow portion 12a of the handle portion 12 and its rear end portion protrudes rearwardly, and a hollow mount insert 32 having internal screw threads 34 near its end portion and a circumferential slot 38 near its external end periphery is threadedly fitted into the rear end portion of the base cylindrical member 18. The front end of fiberscope 30 protrudes slightly out of the opening 12e adjacent the dental tool 16.

The middle connecting means 40 comprises an outer cylindrical member 42 and an inner cylindrical member 50 which is integrally fitted into the cylindrical member 42. The inner cylindrical member 50 has a large diameter front hollow portion 52 and a small diameter rear hollow portion 54 having internal threads 56.

A second passage 60 for introducing air under pressure, a third passage 62 for supplying water and a fourth passage (not shown) for exhaust extend parallel to the central axis of the handpiece through a solid peripheral portion of the inner cylindrical member 50, and radial bores 60a and 62a are provided at the innermost portions of these passages 60 and 62 respectively to intersect the central large diameter front portion 52.

Three radial openings 58, each having a centrally decreasing tapered inner peripheral portion toward the inner end extend through the outer cylindrical member 42 and the inner cylindrical member 50 at the middle portions thereof and also at circumferentially equally spaced locations. A pair of pushed inner ball 86 having a small diameter and a pushing outer ball 84 having a large diameter are slidably positioned in each radial opening 58. A portion of each of these balls 84 and 86 protrudes partially from the corresponding opening.

A radially stepped periphery 68 is provided around the outer periphery of the middle connecting means at its rear end portion. Around the middle outer periphery of the inner cylindrical member 50 is wound a helical spring 70, a rear end of which is urged against the radially periphery 68. Tubes 64 and 66 are integrally inserted into the rear end inlet portions of the second passage 60 and the third passage 62 respectively.

A tubular plunger member 74 having a radially stepped inner peripheral stop element 76 is slidably mounted on the outer cylindrical member 42, thus forming a peripheral space 78 between the inner periphery of the tubular plunger member 74 and the outer periphery of the inner cylindrical member 50. A front end of the helical spring 70 is urged against the radially stepped peripheral stop element 76 of the tubular plunger member 74. A forwardly facing inclined inner surface 80 merges into an inner cylindrical surface 82, the plunger member normally being held in the forward position by spring 70 to push balls 84 inwardly to lock balls 86 in groove 38, as shown in FIG. 4.

A first axial central passage 92 for the fiberscope, a second side passage 94 for supplying air under pressure, a third side passage 96 for supplying water, and a fourth side passage for exhaust (not shown) extending parallel to the axis extend through a solid portion of a rear connecting means 90. A stop element 98 is radially formed around an outer periphery of the rear connecting means 90, and external threads 98a are also provided on the stop element 98 and around the outer periphery of the rear end of the connecting means 90.

A cap 100 having internal peripheral threads 102 is threadedly mounted on the outermost end portion of the rear connecting means 90.

A jack 110 is provided in the central passage 92 of the rear connecting means 90, and a plug 108 of a lampholder 106 supporting an electric lamp 104 is inserted into the jack 110 to establish connection between the electric lamp 104 and an electric power source (not shown).

The rear internal portion 12a of the handle portion 12 is so shaped as to form a socket for snugly receiving the middle connecting means 40, and a rear internal portion of the middle connecting means 40 is so formed as to receive a front portion of the rear connecting means 90 and the electric lamp 104.

The dental handpiece 10 is formed by assembling, as shown in FIG. 4, the handle portion 12, the middle connecting means 40 and the rear connecting means 90 so that the rear end portion 30a of the fiberscope 30 is brought in close proximity to the top portion 106a of the electric lamp 104, and the tubes 64 and 66 are snugly inserted into the second and third passages 94 and 96 respectively.

Accordingly, the central fiberscope passages 20, 40a and 92 are aligned, the second passages 22, 60 and 94 for supplying cooling air under pressure are connected, the third passages 24, 62 and 96 are connected, and the fourt passages for exhaust (not shown) are connected to extend through the handle portion 12, the middle connecting means 40 and the rear connecting means 90.

The rear connecting means 90 of this dental handpiece 10 is coupled to an electric power source, air under pressure supply, water supply and exhaust passages respectively.

As a result the disadvantages described earlier in relation to the prior art can be avoided without increasing the length of the handpiece. Since all connections inside the handle are tight, leaks are eliminated to a great extent.

While the invention has been described in a preferred embodiment, it is to be understood that the words which have been used are words of description rather than of limitation and that changes within the purview of the appended claims may be made without departure from the true scope and spirit of the invention in its broader aspects.

We claim:

1. A dental handpiece for connection to a dental unit, comprising:

a handle portion having a power head assembly integrally supported on the front end of said handle portion, said power head assembly having therein an air turbine for driving a dental tool; a base cylindrical member located in the cylindrical hollow interior of said handle portion, said base cylindrical member having a first axial central passage with a fiberscope therein, a second side passage for supplying air under pressure to said air turbine, a third side passage for supplying water to the dental tool and a fourth passage for exhaust of air from said air turbine, the rear end of said fiberscope projecting slightly out of the rear end portion of said first central passage, each of said second, third and fourth passages extending parallel to said axial central passage and being equally peripherally spaced therearound;

a middle connecting means having an outer cylindrical member and an inner cylindrical member which is integrally fitted into said outer cylindrical member, said inner cylindrical member having a large diameter front hollow portion fitting into said handle portion around said base cylindrical member in fluid tight engagement therewith and a small diameter rear hollow portion into which the rear end of said base cylindrical member extends, three further side passages extending parallel to the axis of said cylindrical members in peripheral positions corresponding to the peripheral positions of said three side passages in said base cylindrical member and being in fluid communication with said three side passages, and releasable locking means engaging said base cylindrical member for locking said middle connecting means to said handle portion; and a rear connecting means having a first axial central passage, a still further second side passage for supplying air under pressure, a still further third side passage for supplying water, and a still further fourth side passage for exhaust, said still further passages being aligned with corresponding ones of said further side passages in said middle connecting means, a stop element projecting radially from the outer periphery of said rear connecting means, a jack in said central passage, a lampholder and a lamp inserted into said jack, said lamp projecting into the rear hollow portion of said middle connecting means adjacent the end of said fiberscope, and a cap having internal threads and rotatably mounted around the outer periphery of said rear connecting means over said stop and threadedly engaged with the rear end of said middle connecting means for firmly attaching said rear connecting means to said middle connecting means.

2. A dental handpiece as claimed in claim 1 in which said base cylindrical member has a circumferential slot around the rear end thereof, and said releasable locking means comprises a plurality of peripherally spaced radial openings extending through said outer and inner cylindrical members, each opening having the inner end tapered inwardly and each radial opening having an inner ball having a small diameter in the radially inner end and projecting into said circumferential slot, and each opening having an outer ball having a large diameter in the radially outer end thereof engaged with the inner ball, and a tubular plunger around the outer periphery of said middle connecting means having a tapered inner peripheral surface facing forwardly of said plunger and a cylindrical surface extending rearwardly from said tapered surface for engaging the outer balls and urging them inwardly to push the smaller balls into said circumferential slot and retain them therein, and spring means engaged with said tubular plunger for urging said tubular plunger forwardly with said cylindrical surface engaging said outer balls.

* * * * *